United States Patent
Makarov et al.

(10) Patent No.: US 7,425,699 B2
(45) Date of Patent: *Sep. 16, 2008

(54) MASS SPECTROMETRY METHOD AND APPARATUS

(75) Inventors: Alexander Makarov, Cheshire (GB);
Mark E Hardman, Manchester (GB);
Jae C. Schwartz, San Jose, CA (US);
Michael W. Senko, Sunnyvale, CA (US)

(73) Assignee: Thermo Finnigan LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/832,596

(22) Filed: Aug. 1, 2007

(65) Prior Publication Data
US 2007/0273385 A1 Nov. 29, 2007

Related U.S. Application Data

(63) Continuation of application No. 11/353,759, filed on Feb. 13, 2006, now Pat. No. 7,265,344, which is a continuation of application No. 11/011,310, filed on Dec. 13, 2004, now Pat. No. 6,998,609, which is a continuation of application No. 10/472,917, filed as application No. PCT/GB02/01373 on Mar. 20, 2002, now Pat. No. 6,872,938.

(30) Foreign Application Priority Data

Mar. 23, 2001 (GB) ................................. 0107380.8
Nov. 7, 2001 (GB) ................................. 0126764.0

(51) Int. Cl.
*G01N 27/62* (2006.01)
*H01J 49/00* (2006.01)
*B01D 59/44* (2006.01)

(52) U.S. Cl. ....................... 250/281; 250/282; 250/283; 250/290; 250/292; 324/464

(58) Field of Classification Search ................. 250/282, 250/281, 283, 290, 292
See application file for complete search history.

(56) References Cited

U.S. PATENT DOCUMENTS

| 6,872,938 B2 * | 3/2005 | Makarov et al. | ............ 250/281 |
| 6,995,364 B2 * | 2/2006 | Makarov et al. | ............ 250/290 |
| 6,998,609 B2 * | 2/2006 | Makarov et al. | ............ 250/290 |
| 7,265,344 B2 * | 9/2007 | Makarov et al. | ............ 250/282 |

* cited by examiner

*Primary Examiner*—Nikita Wells
(74) *Attorney, Agent, or Firm*—Charles B. Katz

(57) ABSTRACT

A mass spectrometer 10 comprises an ion source 12 which generates nebulized ions which enter an ion cooler 20 via an ion source block 16. Ions within a window of m/z of interest are extracted via a quadrupole mass filter 24 and passed to a linear trap 30. Ions are trapped in a potential well in the linear trap 30 and are bunched at the bottom of the potential well adjacent an exit segment 50. Ions are gated out of the linear trap 30 into an electrostatic ion trap 130 and are detected by a secondary electron multiplier 10. By bunching the ions in the linear trap 30 prior to ejection, and by focussing the ions in time of flight (TOF) upon the entrance of the electrostatic trap 130, the ions arrive at the electrostatic trap 130 as a convolution of short, energetic packets of similar m/z. Such packets are particularly suited to an electrostatic trap because the FWHM of each packet's TOF distribution is less than the period of oscillation of those ions in the electrostatic trap.

22 Claims, 8 Drawing Sheets

MASS SPECTROMETRY METHOD AND APPARATUS

CROSS-REFERENCE TO RELATED APPLICATIONS

This application is a continuation of U.S. patent application Ser. No. 11/353,759, filed Feb. 13, 2006 now U.S. Pat. No. 7,265,344, entitled "Mass Spectrometry Method and Apparatus", which is a continuation of U.S. patent application Ser. No. 11/011,310, filed Dec. 13, 2004, granted Feb. 14, 2006 as U.S. Pat. No. 6,998,609, entitled "Mass Spectrometry Method and Apparatus", which is a continuation of U.S. patent application Ser. No. 10/472,917, filed Sep. 23, 2003, granted Mar. 29, 2005 as U.S. Pat. No. 6,872,938, entitled "Mass Spectrometry Method and Apparatus," which is a national stage application under 35 U.S.C. § 371 of PCT Application No. PCT/GB02/01373, filed Mar. 20, 2002, entitled "Mass Spectrometry Method and Apparatus," which claims the priority benefit of United Kingdom Patent Application Nos. 0107380.8, filed Mar. 23, 2001 and 0126764.0, filed Nov. 7, 2001, which applications are incorporated herein by reference in their entireties.

FIELD INVENTION

This invention relates to a method and an apparatus of mass spectrometry, and in particular to a method and an apparatus for storage and injection of ions into an electrostatic ion trap.

BACKGROUND OF THE INVENTION

Mass spectrometers have been used to analyse a wide range of materials, including organic substances such as pharmaceutical compounds, environmental compounds and biomolecules. They are particularly useful, for example, for DNA and protein sequencing. In such applications, there is an ever increasing desire for high mass accuracy, as well as high resolution of analysis of sample ions by the mass spectrometer, notwithstanding the short time frame of modem separation techniques such as gas chromatography/mass spectrometry (GC/MS), liquid chromatography/mass spectrometry (LC/MS) and so forth.

One of the new directions in the field of mass spectrometry is the development of mass analysers where ions are dynamically trapped in an electrostatic field. Broadly, these may be divided into two classes: those that employ frequency analysis by image current detection, as disclosed in U.S. Pat. No. 5,880,466 and U.S. Pat. No. 5,886,346, and those that employ time of flight (TOF) separation and ion detection by secondary electron conversion, as is disclosed, for example by H. Wollnik, in J. Mass Spectrom. Ion Proc. (1994), vol. 131, at pages 387-407, and by C. Piadyasa et al., in Rapid Commun. Mass Spectrom. (1999), vol. 13 at pages 620-624. Although the trap fields may be ramped at the beginning of the mass scan, they are typically held very stable during the detection, or TOF separation of ions, and so each of the foregoing mass analysers may be regarded as electrostatic traps (ESTs).

Such EST mass analysers can achieve high and even ultra-high mass resolutions (in excess of 100,000), thus allowing more accurate determination of ion masses. However, they all operate using an inherently pulsed technique and as such the task of coupling to any external continuous ion source is a serious problem.

To improve duty cycle and sensitivity, it is possible to use an external collision quadrupole ion trap for ion cooling and storage between injections. This technique has proved particularly successful when combined with other inherently pulsed techniques such as TOF mass analysis as is described by S. Michael et al., in Rev. Sci. Instrum. (1992) vol. 63, pages 4277 to 4284. Here, ions are accumulated in the trap. As suggested in U.S. Pat. No. 5,572,022, it is possible to control the number of ions in the trap to reduce space-charge effects. Once ions have been stored in the trap, they can be pulsed into the TOF mass analyser by applying high voltages to the (normally grounded) end caps of the trap. In U.S. Pat. No. 5,569,917, the ions are given a simultaneous "push" out of the trap and a "suck" from the TOF mass analyser, so as to improve the efficiency of ion injection into the analyser. The spatially spread ion beam is focussed into a tight pack in the "object" plane of the TOF mass analyser.

Despite these improvements, quadrupole ion traps are still currently a relatively inefficient technique for injecting ions into a mass analyser (down to a few percent), and they also suffer from low space charge capacity due to the limited trap volume.

One approach that has been taken to address these problems is to employ a different type of collisonal storage device known as a linear trap (LT) or RF multipole trap. U.S. Pat. No. 5,179,278 shows such an arrangement, wherein a two-dimensional multipole RF field is generated. The trap of U.S. Pat. No. 5,179,278 is limited by end lenses. Alternatively, the poles of the trap may be split into sections as is shown in U.S. Pat. No. 5,420,425. Both split poles and end caps can be employed together. The elevated voltages on the end lenses or sections limit the ion movement along the axis whilst the RF voltage provides a quasi-potential well in the radial direction. If ions lose enough energy during the first passes through the multipole, then they may be trapped in it and squeezed towards the axis during further collisions. The number of ions in the trap can be controlled using a short pre-scan, a technique disclosed in the above-referenced U.S. Pat. No. 5,572,022. Nevertheless, to inject ions from the LT into the next stage of analysis, the voltage is lowered on the exit lens and the ions in the LT are allowed to flow out of the multipole. This flow typically lasts up to hundreds or even thousands of microseconds. These time scales are compatible with the injection times for quadrupole ion traps (as disclosed in the above-referenced U.S. Pat. No. 5,179,278) or for Fourier Transform Ion Cyclotron Resonance (FTICR) as set out by M. Senko et al in JASMS, (1997), volume 8, pages 970-976. The time scales are also suitable for orthogonal acceleration TOF mass spectrometry, see for example U.S. Pat. No. 6,011, 259, U.S. Pat. No. 6,020,586, and WO99/30350.

Segmented construction of the poles in the LT may be employed, as set out by M. Belov et al, in Analytical Chemistry (2001) volume 73, pages 253-261, to reduce the injection time down to about 300-400 microseconds. The segmented construction of the LT provides an axial field which causes ions to be displaced towards the exit lens.

Even so, such injection times are too long for an electrostatic trap. This is because ESTs require high ion energies (typically 1-2 keV per charge) to achieve dynamic trapping. If injection takes place over hundreds of microseconds, at such energies the process may last for hundreds of ion reflections. Without any collisional cooling inside the electrostatic trap, ion stability may be compromised.

SUMMARY OF THE INVENTION

It is an object of the present invention to provide a method and an apparatus which alleviates these problems with the prior art. In particular, it is an object to provide a method and an apparatus which provides for adequate storage of ions prior to injection of these ions into an electrostatic trap over a timescale compatible with such a device.

According to a first aspect of the present invention, there is provided a method of injection of sample ions into an electrostatic trap, comprising the steps of: (a) generating a plurality of sample ions to be analysed, each of which has a mass-to-charge ratio m/z; (b) receiving the sample ions through a storage device entrance in an ion storage device having a plurality of storage device poles; (c) supplying a trapping voltage to the storage device so as to trap at least a proportion of the received sample ions within a volume p in the storage device, during at least a part of a trapping period, the thus trapped ions each having a kinetic energy $E_k$ such that there is an average kinetic energy $\overline{E}_k$ of the ions in the volume ρ during the trapping period or the said part thereof; (d) supplying a release voltage to the storage device so as to controllably release at least some of the said sample ions contained within the said volume of the storage device from a storage device exit, the release voltage being of a magnitude such that the potential difference then experienced by the ions across the volume ρ is greater than the said average kinetic energy $\overline{E}_k$ during the trapping period or said part thereof, and further wherein the release voltage is such that the strength of the electric field generated thereby at any first point across the volume ρ, upon application of the said release voltage, is no more than 50% greater or smaller than the strength of the electric field generated thereby at any other second point across the volume ρ; (e) receiving those sample ions released from the storage device exit according to the criteria of step (d) through an entrance of an electrostatic trap having a plurality of trapping electrodes, the ions arriving as a convolution of bunched time of flight distributions for each m/z, each distribution having a full width at half maximum (FWHM); and (f) trapping the received sample ions within the electrostatic trap by applying a potential to the electrodes such that the sample ions describe movement having periodic oscillations in at least one direction.

The method of the present invention proposes particular restrictions on the release potential supplied to the storage device which ensures that groups of ions of a given m/z arrive as a tightly focussed "bunch" at or adjacent the electrostatic trap. The two conditions are, respectively, that the electric field experienced by the ions upon leaving the storage device is relatively uniform and that the potential drop experienced by the ions upon release is larger than the average thermal (kinetic) energy of the ions when trapped in the storage device, and preferably much larger.

The first condition is a consequence of the effective focussing of ions in time of flight from the storage device and into the electrostatic trap. The focal length, L, is given by $L=\alpha V/E$, where V is the final energy of the ions when released from the storage device, E is the electric field strength, and a is a constant. If the electric field is non-uniform, therefore, along the volume ρ, then ions of the same m/z will be focussed at different lengths L and will not arrive in the same tightly focussed bunch. A variation in the electric field strength of no more than about 30%-50% is preferred.

The second criterion ensures that the thermal energy (i.e., the kinetic energy) of the trapped ions is less than and preferably insignificant relative to the gradient of the potential 'slope' upon which the ions find themselves when the release potential is applied.

In an idealized storage device or ion trap, the ions are all in the same place and leave with exactly the same energy when ejected. This means that they arrive at the same time at any chosen location downstream of the ion trap. In reality, of course, the ions have a range of kinetic energies and start off from different locations within the trap. Hence the ions of the same m/z arrive at different times downstream of the ion trap. The purpose of TOF focussing is therefore to cause ions further back in the trap to 'catch up' with ions ejected from the front of the trap, by ensuring that the ions nearer the front of the trap move more slowly than those leaving later. The release potential is chosen so that the ions are ejected without being affected significantly by the random perturbations of thermal energy spread. Although it is necessary that the potential drop is at least as much as the average kinetic energy, a multiple of two is preferred, of five is more preferable, and at least one order of magnitude is most preferable.

This second condition provides the further advantage that the ions will be relatively energetic upon arrival at or adjacent the electrostatic trap. Electrostatic traps have an energy acceptance window, which is centred at a relatively high energy, so that the ions ejected in accordance with the conditions of the present invention are within that energy acceptance window.

Provided that the foregoing conditions are met, the ions will arrive at the electrostatic trap as a convolution of short, energetic packets of similar m/z. Such packets are ideally suited to an electrostatic trap (and particularly the preferred embodiment of an orbitrap) because the FWHM of each ion packet's TOF distribution for a given m/z ratio is then less than the period of oscillation of those sample ions having that m/z when in the electrostatic trap. In other words, the packets are sufficiently coherent for detection to take place.

In preferred embodiments, the ions are pre-cooled, for example in the storage device. This reduces the thermal energy of the ions and also their energy spread, hence reducing the ratio of kinetic energy to release voltage which is the second prerequisite set out above. Pre-cooling may be achieved by collisional cooling, for example. Furthermore, the trapping voltage may be applied so as to force the ions in the storage device towards the exit thereof. This may either be carried out throughout the trapping period or may, in preference, be carried out only immediately prior to ejection.

To obtain bunching of the sample ions at the electrostatic trap, it is preferable to employ an axially segmented linear trap (LT) as the storage device. A differential, preferably DC, voltage is applied between the two or more segments of the LT so as to force the ion cloud within the LT towards the exit thereof. This procedure may be carried out after trapping and cooling of the sample ions received from an ion source in the storage device, which may be achieved by applying voltages to the pole segments so as to create an axial potential well whose base is in the middle of the LT. Alternatively, the bottom of the potential well may be located from the outset at or towards the exit from the storage device. It is particularly preferable that the bottom of the potential well is no more than twice the diameter inscribed by the poles of the storage device away from the storage device exit.

The ions in the storage device are preferably gated out of the exit thereof by applying one or more voltage pulses, to an end electrode of the storage device for example.

The condition for correct focussing or bunching of the sample ions at or adjacent the electrostatic trap is met, in preferred embodiments, by the requirement that the period of oscillation of those ions when injected into the electrostatic trap is shorter, and preferably much shorter, than the time of flight of those sample ions between the storage device exit and arrival at the electrostatic trap entrance.

In alternative embodiments, the further condition that the FWHM time of flight distribution of the ions arriving at the electrostatic trap should be less than the TOF along each detection electrode in the electrostatic trap is imposed as well.

In a particularly preferred embodiment, the storage device is arranged to receive ions along a first direction and to release them from the storage device along a second, orthogonal direction. This permits much higher space charge capacity and better ion beam parameters.

In that case, it is preferable that the storage device should be curved along the first direction. This improves geometric focussing. Optionally, lenses may be added to convert a wide angle beam into a narrow beam.

The method may also include boosting the ion energies prior to their arrival at the electrostatic trap entrance.

In preferred embodiments, the method is employed for the generation, storage and detection of sample ions in MS-only mode. Alternatively, the method may be employed for collision-induced dissociation of the ions to produce daughter sample ion fragments. In either case, it is preferable to select the release voltage so as to focus the ions on the entrance to the orbitrap. In an alternative embodiment, however, the method may be employed to detect fragment ions using surface-induced dissociation. In this case, the method preferably further comprises focussing the sample ions through the electrostatic trap and onto a collision surface. The fragment ions which result are then accelerated back towards the electrostatic trap.

It is particularly preferable that the ions arrive at the electrostatic trap at an angle tangential to a central plane of the electrostatic trap. This is preferably achieved by lenses between the ion trap and the electrostatic trap. The benefit of this is that no further excitation of the ions is necessary once they enter the electrostatic trap. This in turn reduces the amount of electronics necessary for correct operation of the electrostatic trap, and is to be compared with the arrangement of U.S. Pat. No. 5,886,346 referenced above.

The lenses between the ion trap and electrostatic trap, where present, preferably offer no direct line of sight between the inside of the ion trap and the inside of the electrostatic trap. This arrangement prevents streaming of ions and gas carryover from the (relatively high pressure) ion trap into the (relatively lower pressure) electrostatic trap.

Detection of the sample ions in the electrostatic trap may be achieved in a number of ways. Most preferably, the electrostatic trap is of the orbitrap type and ions are trapped in a hyper-logarithmic field. As bunches of coherent ions of different m/z pass by the outer electrodes of the orbitrap, an image current is induced therein. This current may be amplified and then processed to generate a TOF spectrum, for example by Fourier transform analysis.

The field within the electrostatic trap may preferably be compensated by applying a compensating voltage (which may be time dependent) to a field compensator during detection of the ions. This procedure ensures minimum field perturbation within the volume occupied by the ion trajectories. Additionally or alternatively, during ion injection into the electrostatic trap, the field compensator may be arranged to act as a deflector to improve the trapping efficiency of the electrostatic trip.

As with previous ion traps, and LTs in particular, the ion trap may contain facilities for resonance or mass-selective instability scans to provide for data-dependent excitation, fragmentation or elimination of certain m/z ratios.

The optimum duration of ion trapping in the ion trap may be determined prior to commencement of mass analysis by carrying out a pre-scan. Preferably, a secondary electron multiplier (SEM) or the like is employed. The SEM may be located radially of the ion trap and in that case mass-selective instability or a resonance excitation scan in the ion trap may be used. Most preferably, however, an axial SEM is employed downstream of the electrostatic trap and on an ion beam axis. In this case, ions are preferably injected into the electrostatic trap just as they would be for subsequent mass analysis.

According to a second aspect of the present invention, there is provided a mass spectrometer comprising: (a) an ion source arranged to supply a plurality of sample ions to be analysed, each of which has a mass-to-charge ratio m/z; (b) an ion storage device comprising a plurality of storage device poles and having a storage device entrance end through which the said sample ions are received and a storage device exit end through which the said sample ions may exit; (c) a voltage source arranged to supply a trapping voltage to the storage device poles so as to contain at least a proportion of the sample ions received through the storage device entrance end of the storage device within a volume ρ of the storage device in a trapping mode during at least a part of a trapping period, the thus trapped ions each having a kinetic energy $E_k$ such that there is an average kinetic energy $\overline{E}_k$ of the ions in the volume ρ during the trapping period or the said part thereof, and to supply a release voltage to the storage device in an ion ejection mode so as to controllably release at least some of the said sample ions contained within the said volume ρ of the storage device through the storage device exit end, the release voltage being of a magnitude such that the potential difference then experienced by the ions across the volume ρ is greater than the said average kinetic energy $\overline{E}_k$ during the trapping period or said part thereof, and further wherein the release voltage is such that the electric field generated thereby at any first point across the volume ρ, upon application of the said release voltage, is no more than 50% greater or smaller than the electric field generated thereby at any other second point across the volume ρ; and (d) an electrostatic trap having an electrostatic trap entrance arranged to receive those ions released through the storage device exit end and meeting the criteria imposed by the applied trapping and release potentials, as a convolution of bunched time of flight distributions for each m/z, each distribution having a full width at half maximum (FWHM); the electrostatic trap further comprising a plurality of electrodes arranged to trap ions received through the electrostatic trap entrance therebetween so that the said trapped ions describe movement having periodic oscillations in at least one direction.

As with the method of the first aspect, a segmented multipolar ion trap is preferable. In that case, to maximise focussing or bunching of ion packets at the entrance to the electrostatic trap, the length of the segment of the pole pieces proximal the ion trap is preferably shorter than twice the inscribed diameter between the segments of the ion trap (measured radially), and most preferably shorter than the inscribed diameter. Also, the distance between the ion trap exit and the centre of the segment closest thereto is preferably greater than or equal to the said inscribed diameter.

Other features and advantages of the invention will become apparent with reference to the appended claims and to the following specific description.

BRIEF DESCRIPTION OF THE DRAWINGS

The present invention may be put into practice in a number of ways, and some specific embodiments will now be described by way of example only and with reference to the accompanying drawings in which.

DETAILED DESCRIPTION

Figure 1:
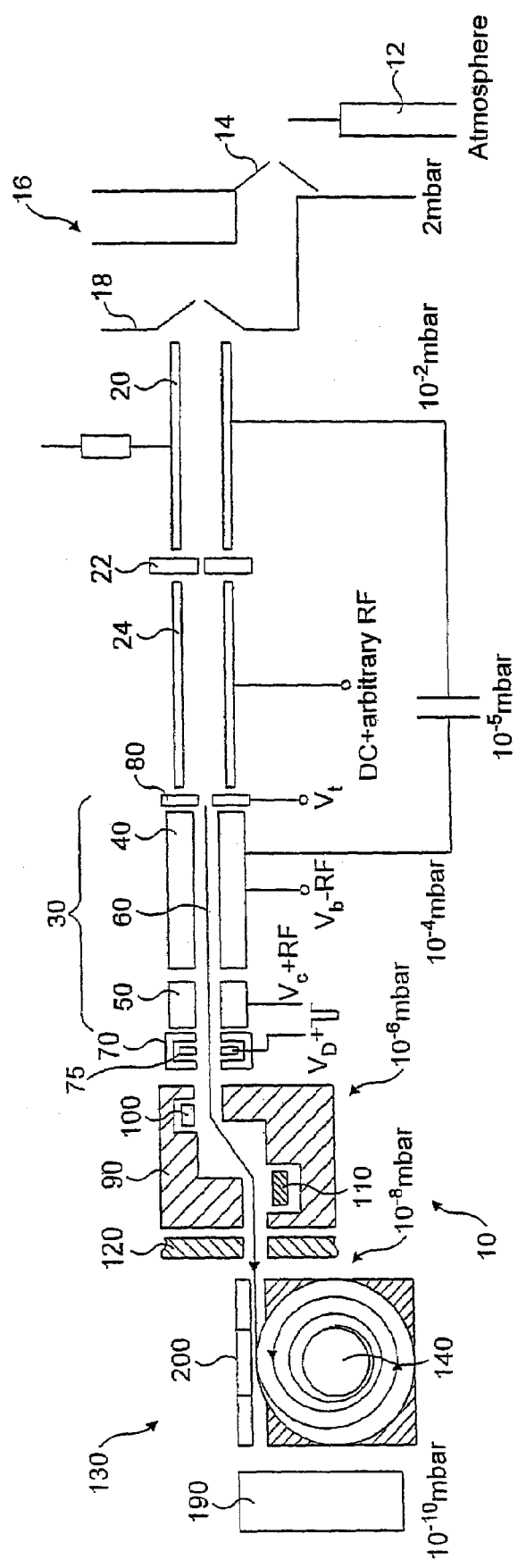
FIG. 1 is a schematic side view of a mass spectrometer embodying the present invention and including an ion trap and electrostatic trap.

Referring first to FIG. 1, a mass spectrometer 10 is shown. The mass spectrometer comprises a continuous or pulsed ion source 12, such as an electron impact source, an electro-spray source (with or without a collisional RF multipole), a matrix-assisted laser desorption and ionisation (MALDI) source, again with or without a collisional RF multipole, and so forth. In FIG. 1, an electrospray ion source 12 is shown.

The nebulized ions from the ion source 12 enter an ion source block 16 having an entrance cone 14 and an exit cone 18. As is described, for example, in WO 98/49710, the exit cone 18 has an entrance at 90° to the ion flow in the block 16 so that it acts as a skimmer to prevent streaming of ions into the subsequent mass analysis components.

A first component downstream of the exit cone 18 is an ion cooler 20 which reduces the energy of the sample ions from the ion source 12. Cooled ions exit the ion cooler 20 through an aperture 22 and arrive at a quadrupole mass filter 24 which is supplied with a D.C. voltage upon which is superimposed an arbitrary r.f. signal. This mass filter extracts only those ions within a window of m/z of interest and the chosen ions are then released to a linear ion trap 30. The ion trap 30 is segmented, in the embodiment of FIG. 1, into an entrance segment 40 and an exit segment 50. Although only two segments are shown in FIG. 1, it will be understood that three or more segments could instead be employed. As better seen in FIG. 2, the segments 40, 50 are each formed from four rods which are radially spaced so as to form a trapping volume 60 between them.

To trap ions within the trapping volume 60, a voltage source (not shown) applies an RF voltage to each of the segments 40, 50. The application of an RF field generates a potential well in the axial direction. Collisions between ions entering the linear trap 30 rapidly cause these ions to sink towards the bottom of the potential well.

The ends of the linear trap 30 are bounded by exit and entrance electrodes 70, 80 respectively. These electrodes are supplied with a DC voltage $V_D$ and $V_a$ respectively. As will be familiar to those skilled in the art, the linear trap 30 may also contain facilities for resonance or mass-selective instability scans, to provide data-dependent excitation, fragmentation or elimination of selected mass-to-charge ratios.

Figure 2:
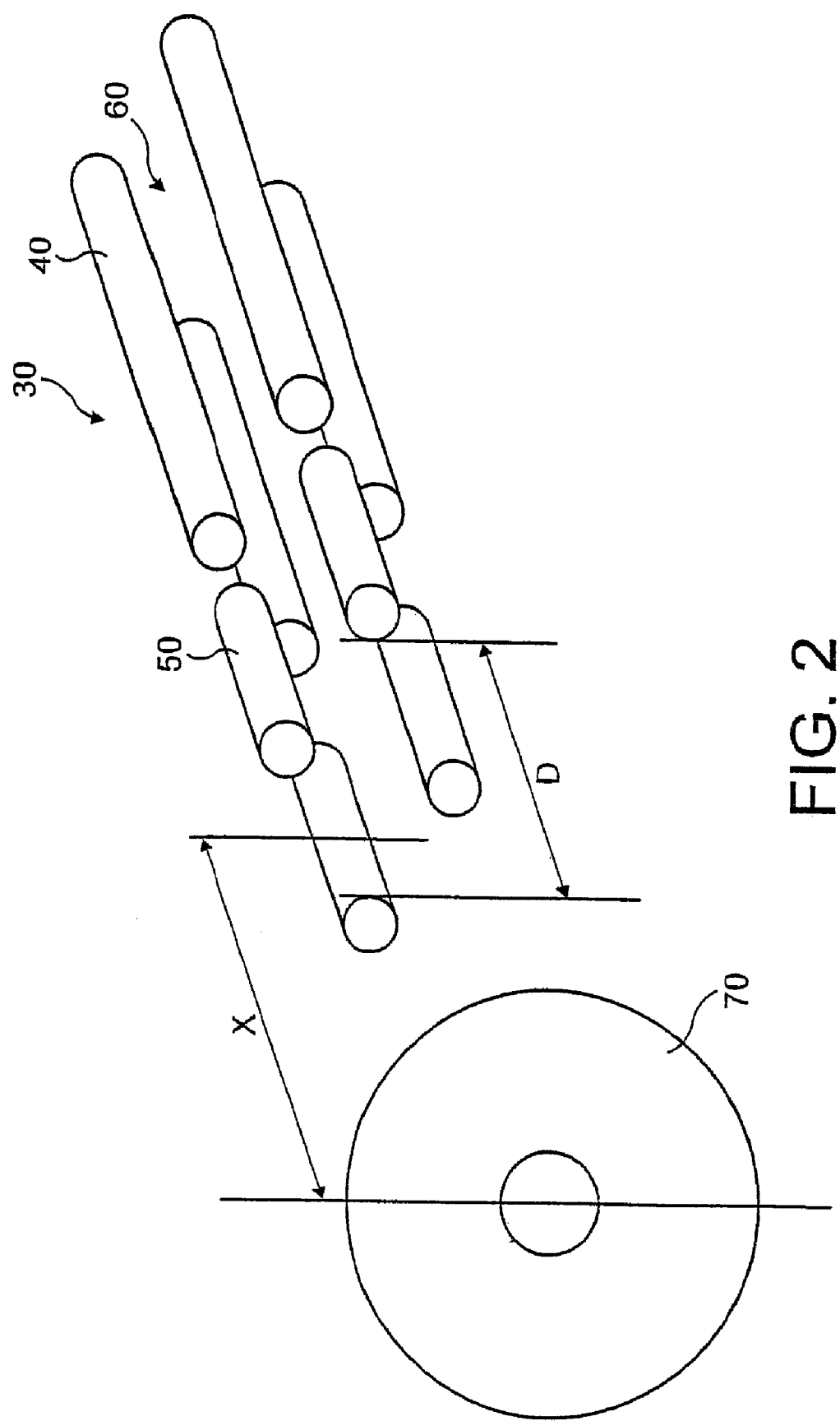
FIG. 2 shows schematically and in perspective a part of the ion trap of FIG. 1.

In preference, the length of the exit segments 50 is not in excess of the inscribed diameter D between the rods (FIG. 2). Also, the distance x between the exit electrode 70 and the axial centre of the exit segment 50 is preferably comparable to, or greater than, the inscribed diameter D (again, see FIG. 2).

The linear trap 30 may have a pressure gradient therein. In this way, the conditions in one part of the trap 30 are optimised for the best dissipation of energy through ion collisions, whilst near the exit electrode 70, the conditions may be optimised for the best trapping, lowest fragmentation and so forth. The pressure gradient may, for example, be created through the introduction of additional gas inlets.

Downstream of the exit electrode is a deflection lens arrangement 90 including deflectors 100, 110. The deflection lens arrangement is arranged to deflect the ions exiting the linear trap 30 in such a way that there is no direct line of sight connecting the interior of the linear trap 30 with the interior of an electrostatic orbitrap 130 downstream of the deflection lens arrangement 90. This prevents streaming of energetic ions from the relatively high pressure linear trap 30 into the relatively low pressure orbitrap 130. The deflection lens arrangement 90 also acts as a differential pumping aperture.

Downstream of the deflection lens arrangement 90 is a conductivity restrictor 120. This sustains a pressure differential between the orbitrap 130 and the lens arrangement 90.

Ions exiting the deflection lens arrangement 90 through the conductivity restrictor 120 arrive at the orbitrap 130. The orbitrap 130 has a central electrode 140 as may better be seen with reference now to FIG. 3. The central electrode 140 is connected to a high voltage amplifier 150.

The orbitrap 130 also contains an outer electrode split into two outer electrode parts 160, 170. Each of the two outer electrode parts 160, 170 is connected to a differential amplifier 180. Preferably, this differential amplifier is maintained at virtual ground.

Referring once more to FIG. 1, downstream of the orbitrap 130 is a secondary electron multiplier 190, on the optical axis of the ion beam. Although not shown in FIG. 1, the secondary electron multiplier (SEM) 190 may also be located on the side of the linear trap 130.

The system, and particularly the voltages applied to the various parts of the system, is controlled by a data acquisition system. This data acquisition system is in itself known and does not form a part of the present invention. Accordingly, it is not shown in the Figures and will not be described further. The data acquisition system may also carry out signal processing as described below. Likewise, a vacuum envelope is also provided, to allow differential pumping of the system. Again, this is not shown in the Figures, although the typical pressures are indicated in FIG. 1.

In operation, ions from the ion source 12 enter the segmented linear trap 30 and are reflected by an elevated potential $V_D$ on the exit electrode 70 thereof. AC voltages at RF frequencies are applied to the segments of the trap to provide a quasi-potential well in the radial direction whilst DC voltages $V_a$, $V_b$ and $V_c$ provide a potential well along the axis of the linear trap 30. The pressure inside the linear trap 30 is chosen in such a way that ions lose sufficient kinetic energy during their first pass through the trap that they accumulate near the bottom of the axial potential well. Before ions are removed from the linear trap 30, the DC voltages $V_a$, $V_b$, $V_d$ and $V_D$ may be varied in such a way that the centre of ion cloud within the linear trap 30 is shifted into the end section of the linear trap, that is, into the volume defined between the rods in the exit segment 50 adjacent to the exit electrode 70. As an alternative, the bottom of the axial potential well may instead be located in this exit segment 50 from the start of ion storage in the linear trap 30.

Figure 4A:
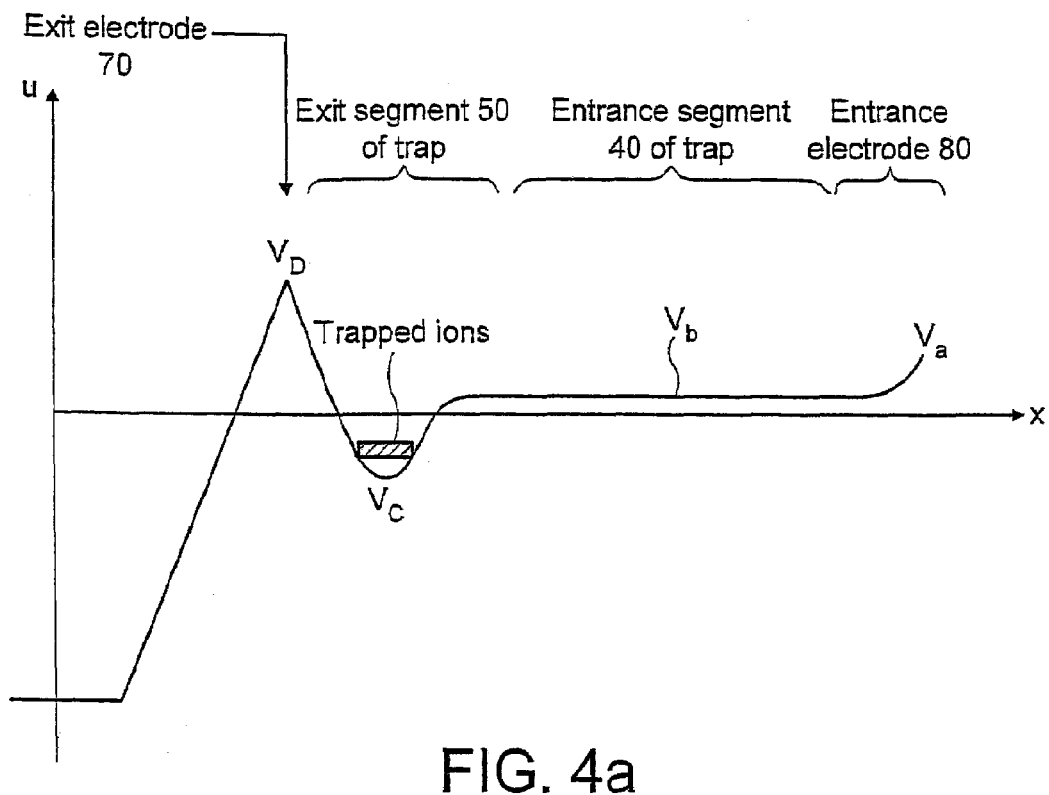
FIG. 4a shows, schematically, the potential distribution in the ion trap of FIGS. 1, 2 and 3 when ions are trapped therein.

FIG. 4a shows, not to scale, the potential electrode 80 and the exit electrode 70 when ions are trapped therein. It will be seen that the ions sit in a potential well defined by the difference in potentials between the exit electrode 70, the exit segment 50 of the trap 30 and the entrance segment 40 thereof.

At the end of storage, the data acquisition system starts to ramp the voltage applied to the central electrode 140 in the orbitrap 130 and, simultaneously, applies a voltage pulse to the exit electrode 70 of the linear trap 30. In presently preferred embodiments, a single pulse is applied to empty the linear trap. However, multiple pulses may be employed instead. In any event, the delay between successive pulses is chosen in such a way that all of the mass range of interest arrives into the orbitrap 130 during the correct phase of the voltage applied to the central electrode 140 thereof as it is ramped. Although the ramping of the voltages on the central electrode of the orbitrap 130 and the exit electrode 70 of the linear trap are timed to each other, they do not however need to be synchronous. Thus, the voltage applied to the central electrode 140 of the orbitrap 130 may start to ramp before the pulse is applied to the exit electrode 70 on the linear trap, and may continue to ramp for a period (e.g. tens of microseconds) after the linear trap has been emptied.

Figure 4B:
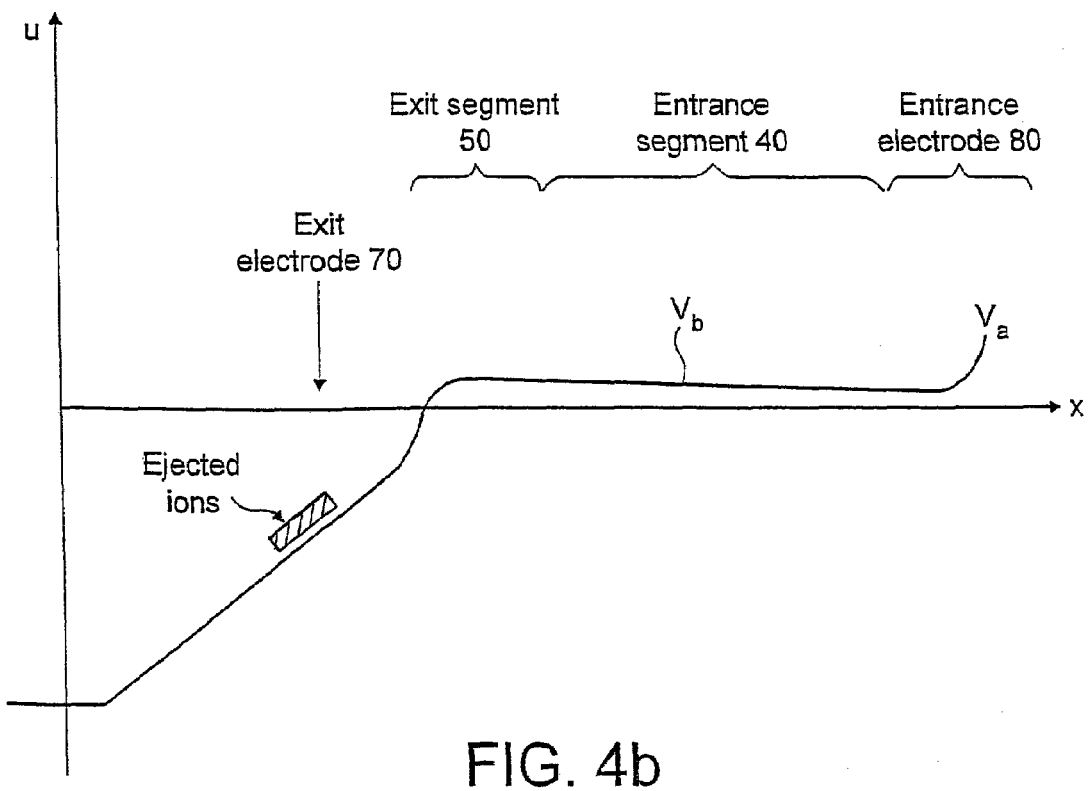
FIG. 4b shows, schematically, the potential distribution in the ion trap of FIGS. 1, 2 and 3 at the point when trapped ions are ejected from the ion trap.

FIG. 4b shows the potential at the different points along the ion trap 30 between the entrance 80 and the exit electrode 70 again not to scale, when such a pulse is applied to the exit electrode 70. Because the pulse is negative (in the convention adapted to illustrate the specific embodiment described, the ions previously trapped in the potential well instantaneously find themselves on a "slope" which accelerates them away from the ion trap 30. As will be explained below, the ejection technique causes the ions leaving the ion trap 30 to be time-of-flight focussed onto the entrance of the electrostatic trap 130.

It is important, for correct trapping of ions in the orbitrap 130, that they arrive at the entrance to the orbitrap when the voltage on the central electrode 140 thereof is between approximately $(D_1/D_2)^{1/2}V$, and V, where V is the final, static voltage on the central electrode 140, $D_1$ is the outer diameter of the central electrode 140, and $D_2$ is the inner diameter of the outer electrode formed from the outer electrode parts 160 and 170. The ion energy at the entrance to the orbitrap 130 also needs to lie within a certain range.

Whilst the voltage applied to the central electrode 140 of the orbitrap 130 is ramped, ions are directed and focussed by the linear trap 30 and the deflection lens arrangement 90 to the entrance of the orbitrap 130. The ions enter the field within the orbitrap 130 tangentially to the outer electrodes formed from the outer electrode parts 160, 170 and are prevented from hitting this electrode again by a monotonically-increasing electric field, which squeezes the ions closer to the centre of the trap. Tangential injection into the orbitrap 130 is achieved by displacing the trap relative to the centre of the beam of ions arriving from the ion trap 30. By way of example only, the orbitrap 130 may be positioned so that ions enter it at a radius of 17.4 mm with z=10 mm, the highest internal radius of the electrodes being 20 mm in this specific example.

The rise time of the electric field depends on the mass range to be trapped, ion parameters, and the orbitrap 130, but is usually between 20 and 200 microseconds. Squeezing stops when there is no more threat of losing ions onto the electrodes.

The orbitrap 130 is shaped so as to generate a hyper-logarithmic field between the central electrode 140 and the outer electrode formed from the outer electrode parts 160, 170. The potential distribution of this hyper-logarithmic field may be described in cylindrical coordinates (r, z) by the following equation:

$$V(r, z) = \frac{k}{2}\left[z^2 - \frac{r^2}{2}\right] + \frac{k}{2}(R_m)^2 \ln\left[\frac{r}{R_m}\right] + C$$

where z=0 is the plane of symmetry of the field, C, k, $R_m(>0)$ are constants, and k>0 for positive ions. Such a field creates a potential well along the z axis direction which causes ion trapping in that potential well provided that the incident energy is not too great for the ion to escape. As the voltage applied to the centre of electrode 140 increases, the field intensity increases and therefore the force on the ions towards the longitudinal axis increases, thus decreasing the radius of spiral of the ions as may be seen from FIGS. 1 and 2. Thus, the ions are forced to rotate in spirals of smaller radius as the sides of the potential well increase in gradient.

There are three characteristic frequencies of oscillation within the hyper-logarithmic field. The first is the harmonic motion of the ions in the axial direction where they oscillate in the potential well with a frequency independent of energy in this direction. The second characteristic frequency is oscillation in the radial direction since not all of the trajectories will be perfectly circular. The third frequency characteristic of the trapped ions is the frequency of angular rotation.

Further details of the preferred electrode arrangement of the orbitrap 130 may be found in U.S. Pat. No. 5,886,346, referenced above, the contents of which are incorporated by reference in their entirety. It will, however, be noted that, in the present case, the ions enter the field tangentially and do not require a separate injection of radial force which in turn reduces the amount of electronic control of the orbitrap 130 that is necessary.

The ion packets arriving at the entrance to the orbitrap 130 are bunched together due to the time of flight focussing created by the ion ejection technique from the linear trap 130. The ion packets are sufficiently coherent that coherent axial oscillation within the orbitrap 130 takes place without addition excitation. The required degree of coherency depends on the type of detection.

If all ions of the same mass-to-charge ratio were to have the same initial kinetic energy, begin flight at the same time, and from the same position within the trap, then they would all leave the trap together and travel together to arrive at exactly the same moment at any point downstream of the trap. This idealized situation cannot of course be realized in practice, primarily due to three factors which 'smear' the initial peak from a delta function. Firstly, the starting position of different ions of the same mass-to-charge ratio will be different, secondly, the time at which flight begins, and thirdly the initial kinetic energies of the different ions of the same mass-to-charge ratio will be different.

The present invention addresses the non-ideal nature of the ions in the trap by firstly minimizing the spread of initial kinetic energies and by 'bunching' the ions together at one end of the trap (so that they tend to leave from roughly the same point in the trap) and secondly by focussing the ions during flight so that any temporal, spatial or energetic spread which still remains is reduced. FIG. 4b shows why this should be so.

When the exit electrode 70 receives the negative going pulse to eject the ions, those ions of the same m/z, which at the moment of pulsing are closest to the exit electrode 70, experience a smaller voltage drop than those further away from the exit electrode 70. As the ions of similar m/z which are closest to the exit aperture have a smaller distance to travel to that exit aperture, they pass through it earlier than the ions 'behind' them but at a lower velocity. In other words, ions further away from the exit aperture 70 on application of the negative pulse take longer to be emptied from the tap but leave it at a higher velocity. In this manner, the ions bunch up downstream of the ion trap 30. By carefully selecting the ejection parameters, the ions in the ion trap 30 may be focussed onto the entrance of the orbitrap 130.

Figure 3:
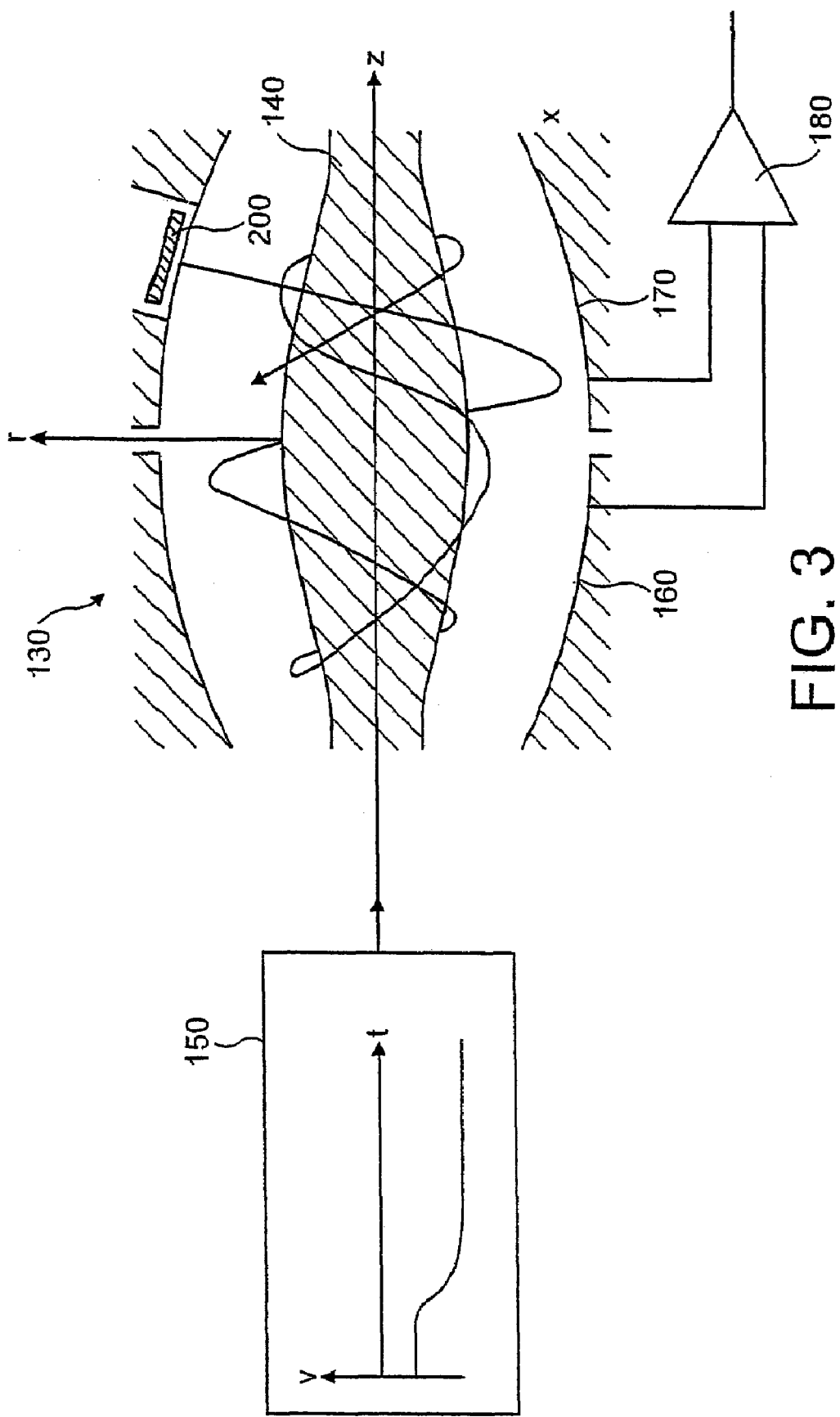
FIG. 3 shows a front view of the electrostatic trap of FIG. 1.

In the preferred embodiment shown in FIGS. 1 and 3, a mass spectrum is generated using image current detection, which technique is again described in U.S. Pat. No. 5,886, 346. An interference pattern of frequencies of different mass-to-charge ratios produces an image current on the outer electrode parts 160, 170. This current is amplified by the differential amplifier 180 and then processed by the data acquisition system by application of a Fourier transform. For this type of ion detection, coherency of the ion packets is achieved as soon as the duration dT (m/z) of a given ion packet of a specific m/z is smaller than the period of axial oscillations within the orbitrap 130. This period of axial oscillation may in turn be significantly less than the time of flight between the linear trap 30 and the entrance to the orbitrap 130. To achieve this level of coherence, time of flight focussing or bunching of the ions as they enter the orbitrap 130 is necessary. It is important to distinguish this bunching from first or second order focussing typical in time of flight (TOF) mass analysers. The time of flight between the linear trap 30 and the orbitrap 130 is normally significantly greater than the period of axial oscillations within the orbit trap 130 because of the differential pumping between the linear trap 30 and the orbitrap 130 which necessarily requires a significant spatial separation between the linear trap and the orbitrap 130.

The electric field strength and the ion trap dimensions are chosen in such a way that the ions catch up, that is, focus in time of flight, just at the entrance to the EST 130. For example, for a uniform field, the focal point is located 3.d away from the starting point where d is the length of this uniform field as measured from the starting point to the field boundary. Non-uniform fields have focussing properties but the mathematical relations are very complex. The random energy distributions of the ions trapped in the ion trap 30 adversely affect the quality of the TOF focussing; for example, the pulse width becomes comparable with the total time of flight as soon as the energy spread of the ions becomes comparable with the acceleration voltage. In order to address these problems, therefor, the bunching of the ions is achieved, in practice, through a combination of the following requirements.

Firstly, the relative variation of the electric field strength along the ion cloud within the ion trap 30, or at least the portion to be injected into the orbitrap 130, should be smaller than unity, and preferably much smaller than unity (such as 10% or even less). Such uniformity of the field along the beam may be achieved by ion squeezing prior to pulsing of the linear trap 30 which in turn is achieved by moving the base of the potential well in the linear trap 30 towards the exit electrode 70 as described above. Collisional cooling of ions within the linear trap also assists in this squeezing. Secondly, the voltage drop across the ion cloud in the linear trap should at least exceed the average kinetic energy during storage, and preferably exceed it by an order of magnitude or more. Such considerable field strength reduces the time of flight spread caused by the initial energies.

The optimum duration of trapping of ions within the linear trap 30 may be determined using a pre-scan after a short storage duration. The secondary electron multiplier 190 allows detection. Where the SEM 190 is located radially of the linear trap 30, mass-selective instability or a resonance excitation scan in the linear trap 30 may be used. It is preferable, however, to use an axial SEM 190, after the orbitrap 130, so that ions are injected in the same way as for the analysis in the orbitrap 130. It will be understood by those skilled in the art that any other known way of ion detection could be used instead of SEM 190, such as a collector with a charge-sensitive amplifier, a photo-multiplier, semiconductor detectors and so forth.

During detection of ions in the orbitrap 130, an appropriate voltage, which may be time-dependent, may be supplied to a field compensator 200 adjacent the entrance to the orbitrap 130. This field compensator ensures minimum field perturbation within the volume occupied by the ion trajectories. During ion injection, this field compensator 200 acts also as a deflector to improve trapping efficiency within the orbitrap 130.

Although a preferred embodiment has been described, it will be understood that various modifications are contemplated. For example, although a linear ion trap 30 has been described for storage of the sample ions from the ion source 12, it is to be understood that a quadrupole ion trap could equally be employed for ion storage, cooling and so forth. Quadrupole ion traps are known as such and one example is shown in EP-A-0,113,207.

Figure 5:
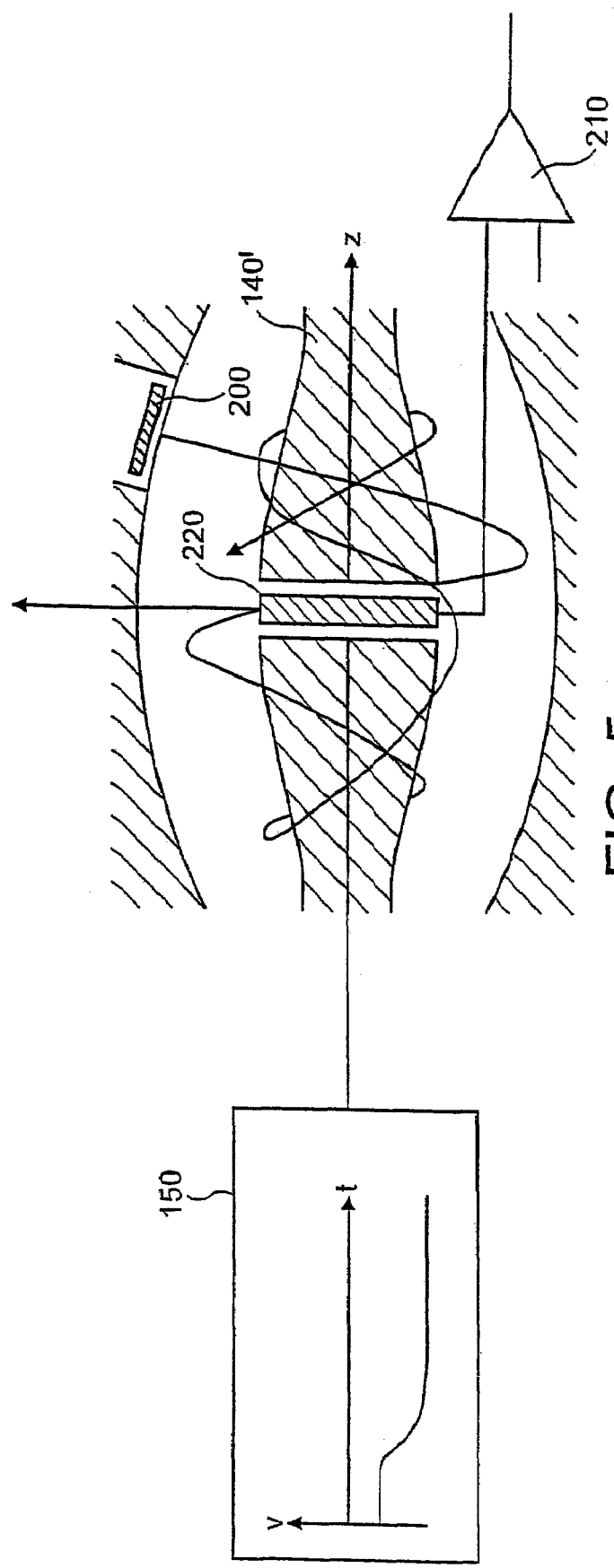
FIG. 5 shows a front view of an alternative electrostatic trap for use in the mass spectrometer of FIG. 1.

Furthermore, a second form of orbitrap 130, seen in front view in FIG. 5, may be employed instead of the one shown in FIG. 3. Here, instead of split outer electrode parts, the outer electrode is not split. Instead, the central electrode 140' is axially segmented with a centre part 220 connected to a pre-amplifier 210. In this arrangement, pulses of image current from passing ion packets of different m/z are detected by this central, disc-shaped electrode part 220, amplified by the pre-amplifier 210, and then processed to yield a time of flight spectrum. A deconvolution method such as is described by M. May et al, in Analytical Chemistry (1992) vol. 64, pages 1601-1605 could be used, or any other signal reconstruction method. Two or more detection electrodes could also be used. The pre-amplifier could also be a differential pre-amplifier with a second input connected to another detection electrode or simply open-ended to improve common mode rejection. For this type of detection, the best results are achieved when the duration dT (m/z) of each ion packet of a particular m/z is not only smaller than the period of axial oscillations in the orbitrap 130, but also does not exceed the time of flight along each of the detection electrodes.

Furthermore, a mass selective instability scan, such as is described in the above-referenced U.S. Pat. No. 5,886,346 could also be used. In this case, ion injection could be performed also along the central plane of the trap.

Figure 6:
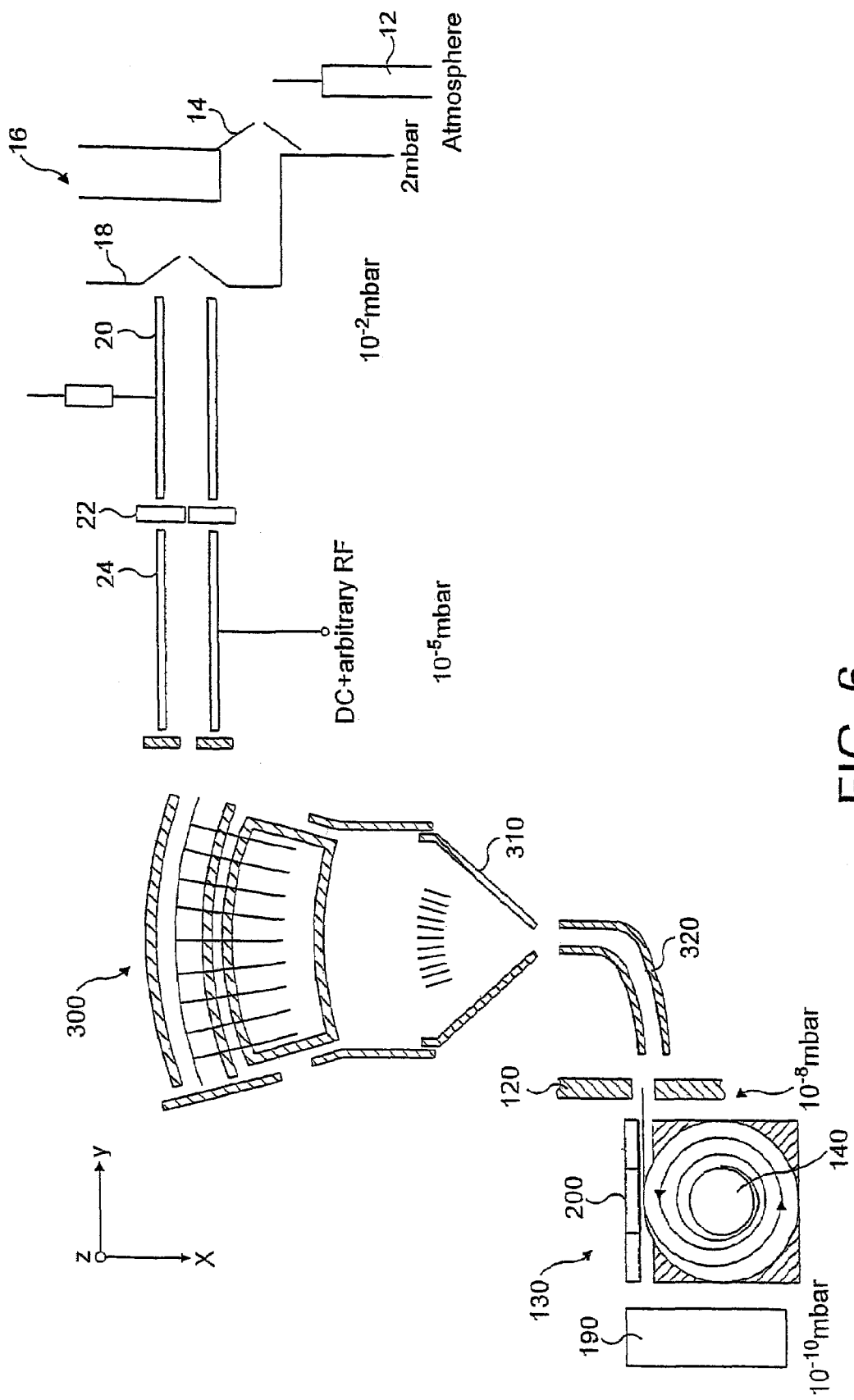
FIG. 6 shows an alternative configuration of the mass spectrometer of FIG. 1, again in schematic side view and including a curved ion trap along with an electrostatic trap.

FIG. 6 shows another mass spectrometer 10' which embodies the present invention and currently represents the preferred implementation. Features common to FIGS. 1 and 6 are labelled with like reference numerals.

As with the arrangement of FIG. 1, the mass spectrometer 10' comprises an electrospray ion source 12 which provides nebulized ions into an ion source block 16 through an entrance cone 14. The ions exit the block 16 via an exit cone 18 and pass into an ion cooler 20 at around $10^{-2}$ mbar. The ions then arrive in a quadrupole mass filter 24 via an aperture 22, and a range of m/z of the incident ions is selected as described previously.

Ions exiting the mass filter 24 enter an ion trap 300 in a first direction generally parallel with a 'y' axis (see FIG. 6). The ions are however ejected from the ion trap 300 in a second direction generally orthogonal to their entrance direction, that is, in an 'x' direction as indicated in FIG. 6. As previously, the ions are focussed in time of flight downstream of the linear trap. Orthogonal ejection of trapped ions additionally allows a much higher space charge capacity than is provided by the arrangement of FIG. 1, and also provides better ion beam parameters.

Although, to achieve orthogonal ejection, a quadrupole assembly such as is shown in FIG. 1 could be used, this requires the RF voltages applied thereto to be switched off instantaneously. This requires very complex associated electronics, however, so, in preference, the ion trap 300 is elongate in the 'y' direction but is curved in the x-y plane (such that the longitudinal axis is likewise curved in the x-y plane). Curvature of the ion trap 300 improves geometrical focussing. By way of distinguishing from the truly linear trap 130 of FIG. 1, the ion trap 300 will henceforth be termed a 'curved trap'.

The curved trap 300 includes lenses 310 extending from the exit of the trap which together convert the wide angle incident beam into a narrow beam.

The narrow ion beam exiting the curved trap 300 passes through a beam deflector 320 and into an electrostatic trap 130. The beam deflector may take one of a variety of forms. A plate in front of the focal point of the focussing lenses could be used to block both ions and gas along the line of sight towards the entrance to the electrostatic trap 130 (for example, around ±5° of arc). Gas arriving from larger angles will not be along the line of sight whereas corresponding ions can be diverted into the electrostatic trap entrance by lenses. The problem with this approach is that it requires the blocking plate to be located in a field-free region which can be difficult to arrange. As an alternative, a toroidal deflector can be employed to achieve the required beam deflection although this introduces extra complexity.

Figure 8:
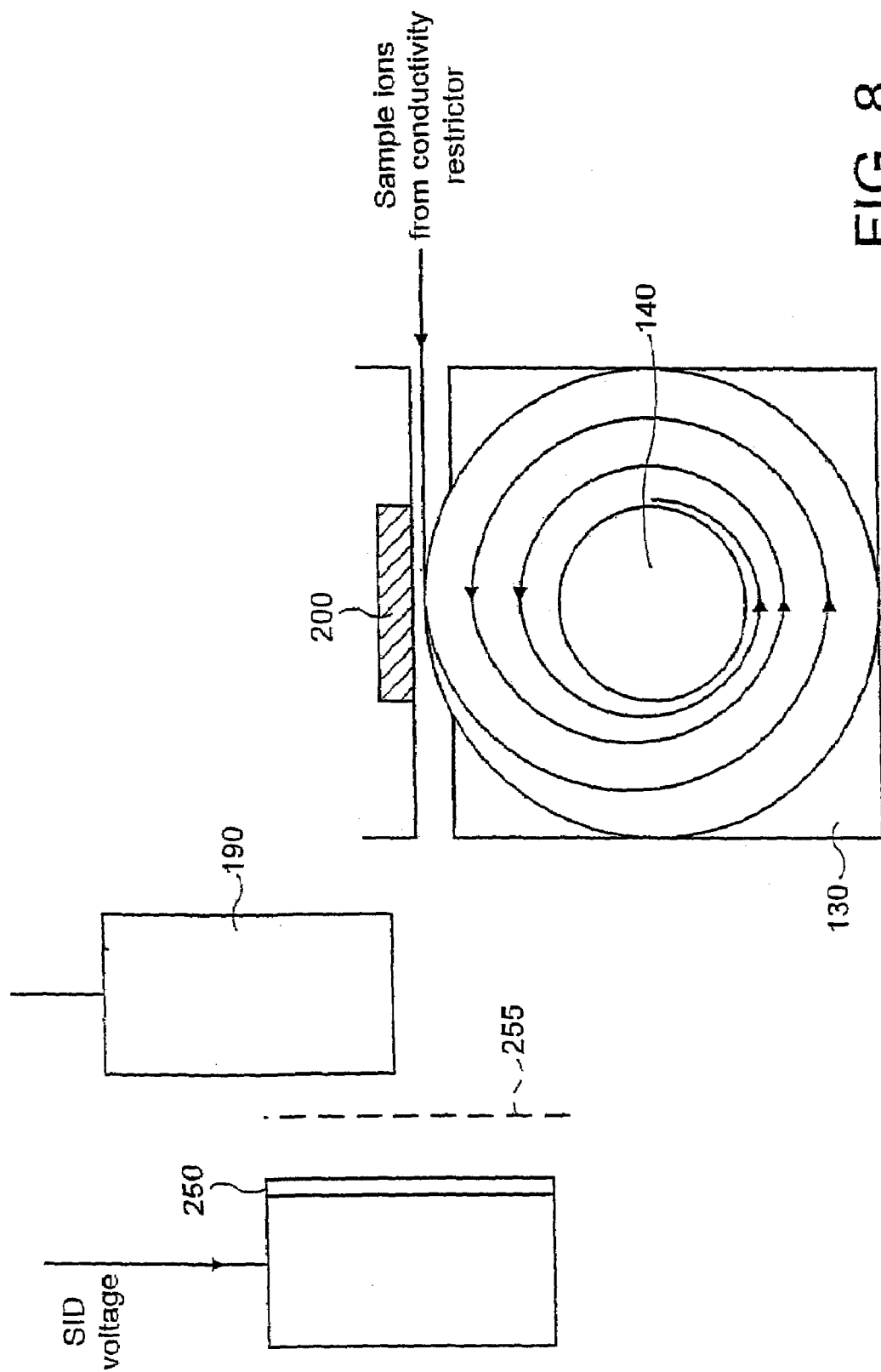
FIG. 8 shows a side view of an electrostatic trap for use with the mass spectrometer of FIG. 1 OR FIG. 6, in combination with a collision surface downstream of the electrostatic trap to allow operation of the mass spectrometer in surface-induced dissociation mode.

The preferred beam deflector 320 is shown in FIG. 6 and contains a right-angled bend which prevents gas carryover along the line of sight between the curved trap 300 and the electrostatic trap 130. An 'S'-shaped beam deflector could of course be employed instead (as is shown in FIG. 1). If the electrostatic trap is arranged with its entrance parallel to the direction of exit of ions from the curved trap 300. As with the arrangement of FIG. 1, the ions are usually focussed in time of flight onto the electrostatic trap entrance which then detects in the manner described previously. However, a different focal point can be chosen, as for example when operating in surface-induced dissociation mode (see FIG. 8 below).

Figure 7:
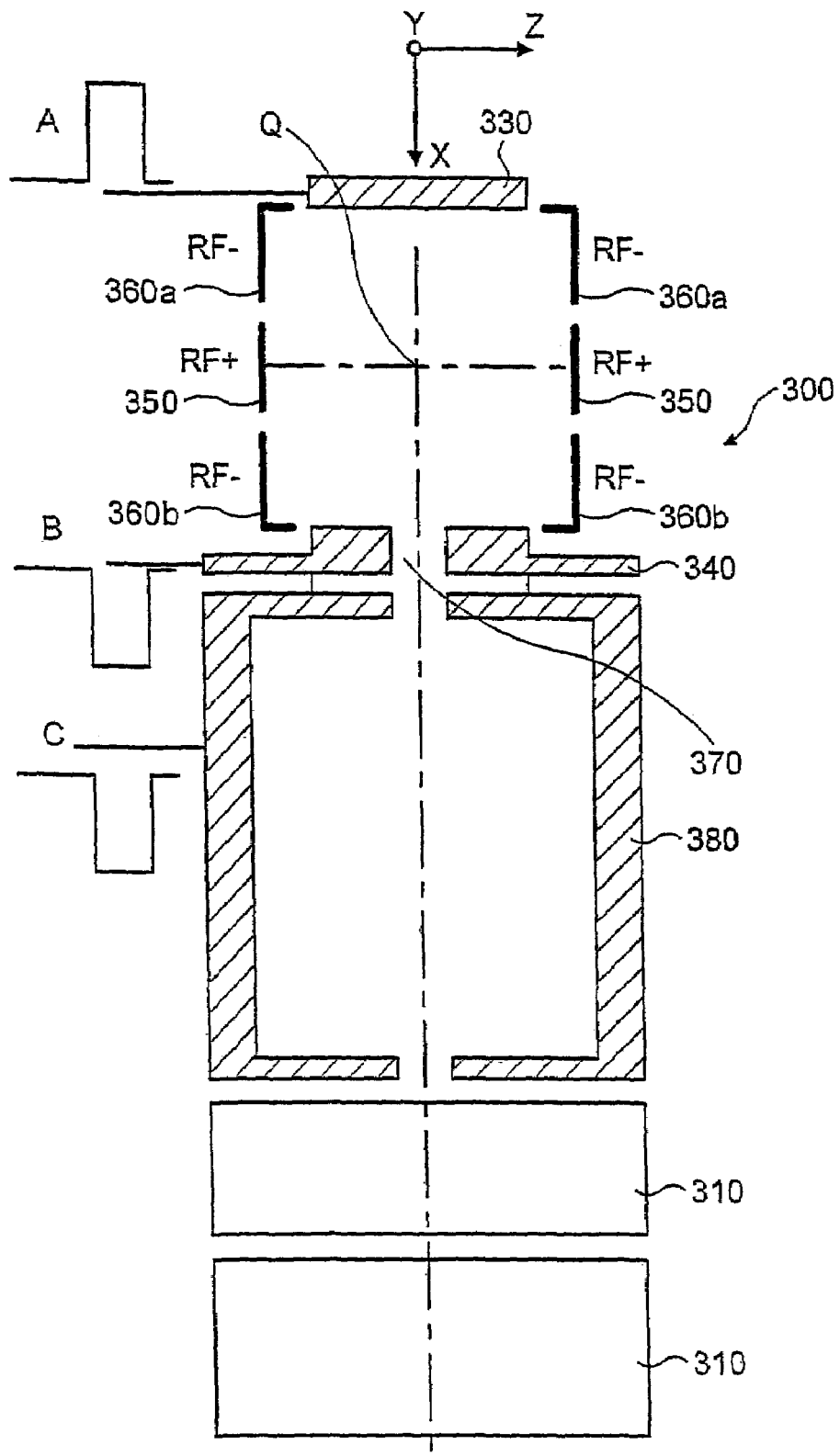
FIG. 7 shows a sectional view through the curved ion trap of FIG. 6.

Referring now to FIG. 7, a sectional view of the curved trap 300 of FIG. 6 is shown. The curved trap 300 is preferably RF only and comprises an outer electrode plate 330, at a D.C. voltage preferably near ground, along with an inner electrode plate 340 at the same D.C. voltage. Sandwiched between the inner and outer electrode plates 330, 340 are upper and lower centre plate pairs 360$a$, 360$b$, to which is applied an RF voltage having a phase indicated on the drawings as RF−. The upper and lower centre plate pairs 360$a$, 360$b$ in turn sandwich an axis plate pair 350 to which is applied an RF voltage (labelled RF+ in FIG. 7) which is in antiphase to the voltage applied to the upper and lower centre plate pairs 360$a$, 360$b$.

The geometry of the curved trap 300 is chosen in such a way that the minimum of the effective potential (that is, the minimum of the RF field) is located exactly in the middle of the trap. This is the axis of symmetry in the plane XZ and is labelled point Q in FIG. 7.

The electrodes 330, 340, 350, 360$a$ and 360$b$ are curved in the XY plane. A DC offset, which is the same as that applied to the inner and outer electrode plates 330, 340, is applied to the upper, lower and axis plates. This causes all masses to be stored in the curved trap 300 and cooled in collisions with gas at 0.1-1 mtorr. At the end of the storage, a positive pulse is applied to the outer electrode plate 330, and a negative pulse of the same amplitude is applied to the inner electrode plate 340 (for positive ions). Ions are extracted by the resulting electric field through a trap exit 370. The RF voltages do not need to be removed as they have little effect on the beam parameters due to their symmetry. In addition, the RF field strength near the X axis is relatively weak. However, it is preferable to time the pulses applied to the inner and outer electrode plates 330, 340 so that they are applied in synchronism with the phase of the RF voltages applied to the upper, lower and axis plates 350, 360$a$, 360$b$.

After sufficient ions have been stored in the trap, they are ejected towards the centre of curvature of the curved trap 300 (see below), and also focussed, both geometrically and in time-of-flight, into a narrow beam that is then introduced into the electrostatic trap 130.

Still referring to FIG. 7, a liner 380 may be provided between the trap exit 370 and the lenses 310. The liner 380 is located in a substantially field-free region of the curved trap. Another pulse, equal to the required ion energy on the entrance to the electrostatic trap 130, may be applied to the liner 380 at the same time as the pulses are applied to the inner and outer electrode plates 330, 340. The pulse is applied to the liner so as to create an "energy lift", that is, to produce a high ion energy in conditions where both the DC offset applied to the curved trap 300 and the potential applied to the outer electrode parts 160, 170 of the orbitrap 130 (FIG. 3) are maintained near ground voltage. If the curved trap 300 floats at the acceleration voltage then no energy lift will be required. Nevertheless, it is important that any ion source should have the capability to float as well.

The length of the liner 380 is defined by the required relative mass range: the ratio of the maximum to minimum masses is given by $m_{max}/m_{min}=(L_1/L_2)^2$, where $L_1$ is the effective distance from the axis to the exit from liner and $L_2$ is the effective distance to the entrance to the liner. The duration of the pulse applied to the liner 380 is determined by calculating the time-of-flight, to the liner exit, for the lightest mass of interest, so that this mass emerges from the liner 380 at its full energy whilst the voltage on the liner 380 is already back to its normal value (near ground). The duration of the pulses applied to the inner and outer electrode plates 330, 340 should be longer than this.

It is to be understood that the liner 380 in the curved trap 300 of FIGS. 6 and 7 is equally suitable for the linear trap 30 of FIG. 1.

The foregoing description of some preferred embodiments has also explained the principles involved with reference to sample ions that are derived directly from an atmospheric pressure ionization source or the like, and are simply stored as such in the ion trap. However, structural analysis of sample ions may also be carried out using TOF focussing and any of the ms/ms modes available. Three modes in particular are contemplated.

In collision-induced dissociation (CID), precursor ions may be selected either by the quadrupole mass filter 24 (FIG. 1) or inside the ion trap 30. Ejection of unwanted ions in each of these cases may be performed, for example, by resonant excitation between the opposite rods of each device or by a mass selective instability scan (see, for example, the above-referenced U.S. Pat. No. 5,886,346). This may be achieved by DC biassing one set of rods relative to the other, for example. Fragmentation may be caused by collisions with collision gas at an elevated pressure in a dedicated RF-only multipole or, preferably, in the linear ion trap 30. The resulting fragments are stored and collisionally cooled in the ion trap 30 and then injected into the orbitrap 130 in the same way as described previously. CID in collisional multipoles is a technique which is well known as such to those skilled in the art and the technique of selecting only the required m/z is likewise a known part of tandem mass spectrometry. Further description of these techniques may be found in "Protein Sequencing and Identification Using Tandem Mass Spectrometry", by M. Kinter, N. E. Sherman, John Wiley and Sons, 2000, and in "Mass Spectrometry/Mass Spectrometry: Techniques and Applications of Tandem Mass Spectrometry", by K. L. Busch, G. L. Glish, and S. A. McLuckey, John Wiley and Sons, 1989.

In surface-induced dissociation (SID), precursor ion selection is typically carried out in the same way as in CID. Precursor ions are stored in the linear trap 30 and then pulsed towards the orbitrap 130. However, in this case the TOF focus is shifted behind the plane of the entrance of the orbitrap 130, to a separate plane where a collision surface is located. This is shown schematically in FIG. 8, which illustrates in side view the orbitrap 130 along with the electrode 140, the compensator 200 and the secondary electron multiplier 190. The collision surface 250 is located downstream of the secondary electron multiplier 190 and may be formed from a metal or may instead be metal- or polymer-coated. A fluorocarbon or hydrocarbon self-assembled monolayer plate such as is disclosed in Science, Vol. 275, pages 1447-1450, by S. A. Miller, H. Luo, S. J. Pachuta and R. G. Cooks, (1997) could for example be used.

In this case, precursor ions pass tangentially through the orbitrap 130, which has electric fields that are low enough to prevent ion losses, and out past the compensator 200 which in this part of the process is switched off to allow passage of the precursor ions. These precursor ions then decelerate in front of the collision surface 250 in a deceleration gap created by a grid 255 and collide with the collision surface 250 at a collision energy determined by a voltage difference between the collision surface and the offset applied to the exit segment 50 of the linear trap. Collision results in the formation of fragment ions at low energies (several electronvolts) which are accelerated by the same electric field towards the orbitrap 130. Due to the TOF focussing of these precursor ions and the instantaneous nature of SID, fragment ions separate (at least partially) on their way to the orbitrap 130 according to their mass/charge ratio and ions of each mass/charge ratio enter the orbitrap 130 as a short packet. The compensator 200 is switched on during this part of the process so that the fragment ions are then captured by the orbitrap. This allows ions to be captured in the same way as in the MS-only mode described in connection with FIGS. 1 to 5 above. If low resolution of parent selection is sufficient for a given application, then an ion gate (not shown) may be installed between the orbitrap 130 and the collision surface 250 to provide an alternative way of selecting precursor ions. It is in fact possible to use the deflection electrode 200 of the orbitrap 130 as an ion gate.

Finally, metastable dissociation (MSD) mode may be employed with the arrangement and principles outlined previously. Precursor ions may either be selected as described above in connection with the CID and SID modes, or may instead be injected into the orbitrap 130 without prior selection. The only difference from the MS-only mode described in connection with FIGS. 1 to 5 is the activation of ions in the ion trap 30. Activation may be achieved by pulsed ion extraction in the presence of gas at an elevated pressure (either static or pulsed), wherein the increase of ion internal energy is controlled by the gas pressure, by pulsed electromagnetic radiation (e.g. infrared radiation which can be used to excite ions inside the ion trap 30, or by resonant or broadband dipolar excitation using at least two pairs of quadrupole rod electrodes in the ion trap 30. In that case, the increase of internal energy is controlled by the amplitude of the excitation signal and the gas pressure.

Although pulsed ion extraction with a high pressure gas is preferable due to its simplicity, each of the foregoing results in the excitation ("heating") of ions and the consequent formation of metastable ions with a controllable decay constant. The magnitude of the decay constant can be controlled by variation of the intensity of excitation. Before fragmentation becomes noticeable, ions may be injected into the orbitrap 130 and precursor ion selection may even be achieved. On the other hand, excessively long decay times lead to a decrease in the speed of analysis. Therefore, optimum decay times range from several milliseconds to tens of milliseconds.

Precursor ion selection is achieved by applying a radio frequency voltage in resonance with the axial oscillation of precursor ions at a correct phase. A waveform generator (not shown), under the control of the data processing system referred to in connection with FIG. 1, supplies this RF voltage either to the central electrode 140 (parametric resonance de-excitation at doubled ion frequency, set out in Analytical Chemistry Volume 72, No. 6, p. 1156-1162, by Makarov, and in the above-referenced U.S. Pat. No. 5,886,346), or between the two outer electrode parts 160, 170 (resonance de-excitation at ion frequency) of the orbitrap 130. Application of an RF voltage decreases the amplitude of axial oscillation of ions so that only precursor ions are brought into the plane of symmetry of the orbitrap 130. Precursor ions are left in this state long enough to allow metastable decay to occur. The remaining precursor ions are then excited, together with their fragment ions, by a broadband excitation. Typically, a radio frequency voltage is applied to the two outer electrode parts 160, 170 by the waveform generator. Coherent oscillations of ions of each mass/charge ratio are detected by detecting an image detection current via the differential amplifier 180 in the same way as described for MS-only mode. Metastable decay of ions other than precursor ions also results in the formation of fragment ions. However, these are uniformly spaced along the orbitrap 130 and thus do not move coherently. No image current is produced for detection in that case. Alternatively, unwanted precursor or fragment ions may be removed by an additional broadband excitation.

What is claimed is:

1. A mass spectrometer, comprising:
an ion source for producing ions from a sample;
a storage device positioned to receive and store ions from the ion source, the storage device being configured to controllably release ions stored therein upon application of a release voltage; and
a mass analyzer positioned to receive ions released from the storage device, the mass analyzer including a set of electrodes operable to generate an electrostatic field that causes ions to undergo periodic oscillations in the mass analyzer.

2. The mass spectrometer of claim 1, wherein the storage device is a linear RF ion trap.

3. The mass spectrometer of claim 2, wherein the linear RF ion trap releases ions stored therein along an axis that is generally orthogonal with respect to an axis along which ions enter the linear RF ion trap.

4. The mass spectrometer of claim 2, wherein the linear RF ion trap is curved along its major axis.

5. The mass spectrometer of claim 4, wherein the linear RF ion trap releases ions stored therein along an axis that is generally orthogonal with respect to an axis along which ions enter the linear RF ion trap.

6. The mass spectrometer of claim 1, wherein the storage device is configured to controllably release only a portion of the ions stored therein, the released ions having a range of mass-to-charge ratios that is narrower than the range of mass-to-charge ratios of the stored ions.

7. The mass spectrometer of claim 1, wherein the storage device is operable to fragment at least a portion of the ions stored therein to produce product ions, and to controllably release the product ions.

8. The mass spectrometer of claim 1, wherein the storage device is divided into a plurality of segments such that each segment is operable to trap a separate population of ions.

9. The mass spectrometer of claim 1, wherein the mass analyzer includes an electrostatic trap analyzer.

10. The mass spectrometer of claim 9, wherein the electrostatic trap analyzer is an orbitrap analyzer.

11. The mass spectrometer of claim 1, further comprising a secondary electron multiplier for detecting ions separated by the mass analyzer.

12. The mass spectrometer of claim 1, wherein the mass analyzer includes a set of electrodes for detecting image current pulses produced by ion motion.

13. The mass spectrometer of claim 1, further comprising an electrode interposed between the storage device and the mass analyzer, the electrode having a voltage pulse applied thereto to control the kinetic energy of ions entering the mass analyzer.

14. The mass spectrometer of claim 1, wherein:
the release voltage has a magnitude such that the potential difference experienced by the ions across a trapping volume of the storage device is greater than an average kinetic energy $\overline{E}_k$ during a trapping period; and
the release voltage is selected such that the electric field generated thereby at any one point across the trapping volume is no more than 50% smaller or greater than the electric field generated thereby at any other point across the trapping volume.

15. A method of analyzing a sample, comprising:
producing ions from the sample;
storing the ions in a storage device; and
controllably releasing the ions, or ions derived therefrom, from the storage device;
receiving the released ions within a mass analyzer; and
generating an electrostatic field within the mass analyzer that causes the ions to undergo periodic oscillations within the mass analyzer.

16. The method of claim 15, wherein the step of controllably releasing the ions includes releasing the ions in a direction generally orthogonal to an axis along which ions enter the storage device.

17. The method of claim 15, wherein the step of controllably releasing the ions includes releasing only ions having a range of mass-to charge ratios narrower than the range of mass-to-charge ratios of the stored ions.

18. The method of claim 15, further comprising the step of fragmenting the ions stored in the storage device to produce product ions.

19. The method of claim 15, further comprising a step of controlling the kinetic energy of the ions released from the storage device prior to their arrival at the mass analyzer.

20. The method of claim 15, further comprising a step of directing ions separated within the mass analyzer to a detector.

21. The method of claim 15, further comprising a step of detecting image current pulses produced by ion motion within the mass analyzer.

22. The method of claim 15, wherein the step of controllably releasing the ions, or ions derived therefrom, from the storage device includes applying a release voltage to the storage device, and further wherein:
the release voltage has a magnitude such that the potential difference experienced by the ions across a trapping volume of the storage device is greater than an average kinetic energy $\overline{E}_k$ during a trapping period; and
the release voltage is selected such that the electric field generated thereby at any one point across the trapping volume is no more than 50% smaller or greater than the electric field generated thereby at any other point across the trapping volume.

* * * * *